United States Patent

Mochizuki et al.

(10) Patent No.: US 10,512,136 B2
(45) Date of Patent: Dec. 17, 2019

(54) ULTRAVIOLET IRRADIATION DEVICE

(71) Applicant: Nikkiso Co., Ltd, Tokyo (JP)

(72) Inventors: Hiroaki Mochizuki, Ishikawa (JP); Ryouta Kawasaki, Ishikawa (JP)

(73) Assignee: Nikkiso Co., Ltd., Tokyo (JP)

( * ) Notice: Subject to any disclaimer, the term of this patent is extended or adjusted under 35 U.S.C. 154(b) by 0 days.

(21) Appl. No.: 16/227,655

(22) Filed: Dec. 20, 2018

(65) Prior Publication Data

US 2019/0200424 A1 Jun. 27, 2019

(30) Foreign Application Priority Data

Dec. 27, 2017 (JP) .................. 2017-251490

(51) Int. Cl.
| H05B 37/02 | (2006.01) |
| H05B 33/08 | (2006.01) |
| A61L 2/24 | (2006.01) |
| A61L 2/10 | (2006.01) |

(52) U.S. Cl.
CPC .............. *H05B 33/089* (2013.01); *A61L 2/10* (2013.01); *A61L 2/24* (2013.01); *H05B 33/0848* (2013.01); *H05B 33/0851* (2013.01); *H05B 33/0854* (2013.01)

(58) Field of Classification Search
CPC ............ H05B 33/0848; H05B 33/0851; H05B 33/0854
USPC ...................................... 315/185 R, 307, 308
See application file for complete search history.

(56) References Cited

U.S. PATENT DOCUMENTS

| 8,618,737 B2 * | 12/2013 | Welten ................. H05B 33/083 315/153 |
| 9,076,357 B2 * | 7/2015 | Hussain ............. H05B 33/0827 |
| 2007/0195025 A1 * | 8/2007 | Korcharz ............. G09G 3/3413 345/82 |
| 2011/0001432 A1 * | 1/2011 | Chung ............... H05B 33/0818 315/152 |

FOREIGN PATENT DOCUMENTS

| JP | 3156000 B2 | 4/2001 |
| JP | 2005-199476 A | 7/2005 |
| JP | 2006-040944 A | 2/2006 |
| JP | 2006-147373 A | 6/2006 |
| JP | 2008-210588 A | 9/2008 |
| JP | 2009-283585 A | 12/2009 |

(Continued)

*Primary Examiner* — Thuy V Tran
(74) *Attorney, Agent, or Firm* — Muncy, Geissler, Olds & Lowe, P.C.

(57) ABSTRACT

An ultraviolet irradiation device includes a light source unit, a drive circuit, a sensing unit and a controller. The light source unit includes a plurality of light emitting devices and outputs ultraviolet light as irradiating light. The drive circuit supplies a drive current (Id) to the plurality of light emitting devices. The sensing unit senses a trouble in the plurality of light emitting devices. The controller controls the drive current (Id) in accordance with a result of sensing by the sensing unit. When an output of the light source unit is reduced due to a trouble in one or some of the plurality of light emitting devices, the controller controls the drive current (Id) of a plurality of light emitting devices other than the light emitting device in trouble so as to compensate reduction in the output of the light source unit.

12 Claims, 6 Drawing Sheets

| 8 TARGET OF IRRADIATION | 12 LIGHT EMITTING DEVICE |
| 10 LIGHT SOURCE UNIT | 16 IRRADIATING LIGHT |
| 20 DRIVE CIRCUIT | 20b CURRENT SOURCE |
| 30 SENSING UNIT | 30b SENSING ELEMENT |
| 40 CONTROLLER | |

100

(56) References Cited

FOREIGN PATENT DOCUMENTS

| | | |
|---|---|---|
| JP | 2012-513106 A | 6/2012 |
| JP | 2013-016694 A | 1/2013 |
| JP | 2015-000111 A | 1/2015 |
| JP | 2016-068052 A | 5/2016 |
| JP | 2017104230 A | 6/2017 |
| JP | 2017-121592 A | 7/2017 |

* cited by examiner

ULTRAVIOLET IRRADIATION DEVICE

RELATED APPLICATION

Priority is claimed to Japanese Patent Application No. 2017-251490, filed on Dec. 27, 2017, the entire content of which is incorporated herein by reference.

BACKGROUND OF THE INVENTION

1. Field of the Invention

The present invention relates to ultraviolet irradiation devices and, more particularly, to a technology of killing microbes, performing a reaction treatment, sensing a substance, etc. by radiating ultraviolet light.

2. Description of the Related Art

Ultraviolet irradiation devices configured to kill microbes, perform a reaction treatment, sense a substance, etc. by irradiating a target of irradiation with ultraviolet light are known. We disclosed a technology of a fluid sterilization device configured to kill microbes by irradiating a fluid with ultraviolet light in JP2017-104230. The fluid sterilization device disclosed in JP2017-104230 is provided with a light source configured to radiate ultraviolet light from one end of an axially extending flow passage tube in the axial direction toward a processing passage defined by the flow passage tube.

We have gained the following knowledge about ultraviolet irradiation devices configured to irradiate a target of irradiation with ultraviolet light. Many of these ultraviolet irradiation devices are provided with a light source that includes a light emitting device configured to emit ultraviolet light. The light emitting function of the light emitting device configured to emit ultraviolet light may be reduced due to a trouble, etc. In the case that a fluid as a target of irradiation is irradiated with ultraviolet light to kill microbes included in the fluid, for example, the sterilization function is lost when the light emitting device is in trouble. When the fluid continues to flow while the light emitting device is in trouble, the fluid insufficiently sterilized may flow toward the downstream side. The condition may last until the trouble is found and fixed.

Thus, in the case that a plurality of light emitting devices are provided and one of the light emitting devices is in trouble, the remaining normal light emitting devices may irradiate the target of irradiation with ultraviolet light. In this case, however, the number of light emitting devices that emit light is reduced. In association with this, the illuminance may be reduced, and the fluid insufficiently sterilized may flow toward the downstream side. Based on the foregoing, we have recognized an issue in that there is room for improvement in ultraviolet irradiation devices configured to irradiate a target of irradiation with ultraviolet light from the perspective of inhibiting reduction in the output of the light source unit when one or some of the plurality of light emitting devices is in trouble.

Such an issue can arise not only in ultraviolet irradiation devices configured to radiate ultraviolet light to kill microbes but also in ultraviolet irradiation devices configured to irradiate a target of irradiation with ultraviolet light for other uses.

SUMMARY OF THE INVENTION

In this background, one illustrative purpose of the present invention is to provide a ultraviolet irradiation device capable of inhibiting reduction in the output of the light source unit when one or some of the plurality of light emitting devices is in trouble.

A ultraviolet irradiation device according to an embodiment includes: a light source unit that includes a plurality of light emitting devices and outputs ultraviolet light as irradiating light; a drive circuit that supplies a drive current to the plurality of light emitting devices; a sensing unit that senses a trouble in the plurality of light emitting devices; and a controller that controls the drive current in accordance with a result of sensing by the sensing unit. When an output of the light source unit is reduced due to a trouble in one or some of the plurality of light emitting devices, the controller controls the drive current of a plurality of light emitting devices other than the light emitting device in trouble so as to compensate reduction in the output of the light source unit.

According to the embodiment, the drive current of a plurality of light emitting devices other than the light emitting device in trouble can be controlled.

Optional combinations of the aforementioned constituting elements, and implementations of the invention in the form of methods, systems, etc. may also be practiced as additional modes of the present invention.

BRIEF DESCRIPTION OF THE DRAWINGS

Embodiments will now be described by way of examples only, with reference to the accompanying drawings which are meant to be exemplary, not limiting and wherein like elements are numbered alike in several Figures in which.

DETAILED DESCRIPTION OF THE INVENTION

The invention will now be described by reference to the preferred embodiments. This does not intend to limit the scope of the present invention, but to exemplify the invention.

First Embodiment

Figure 1:
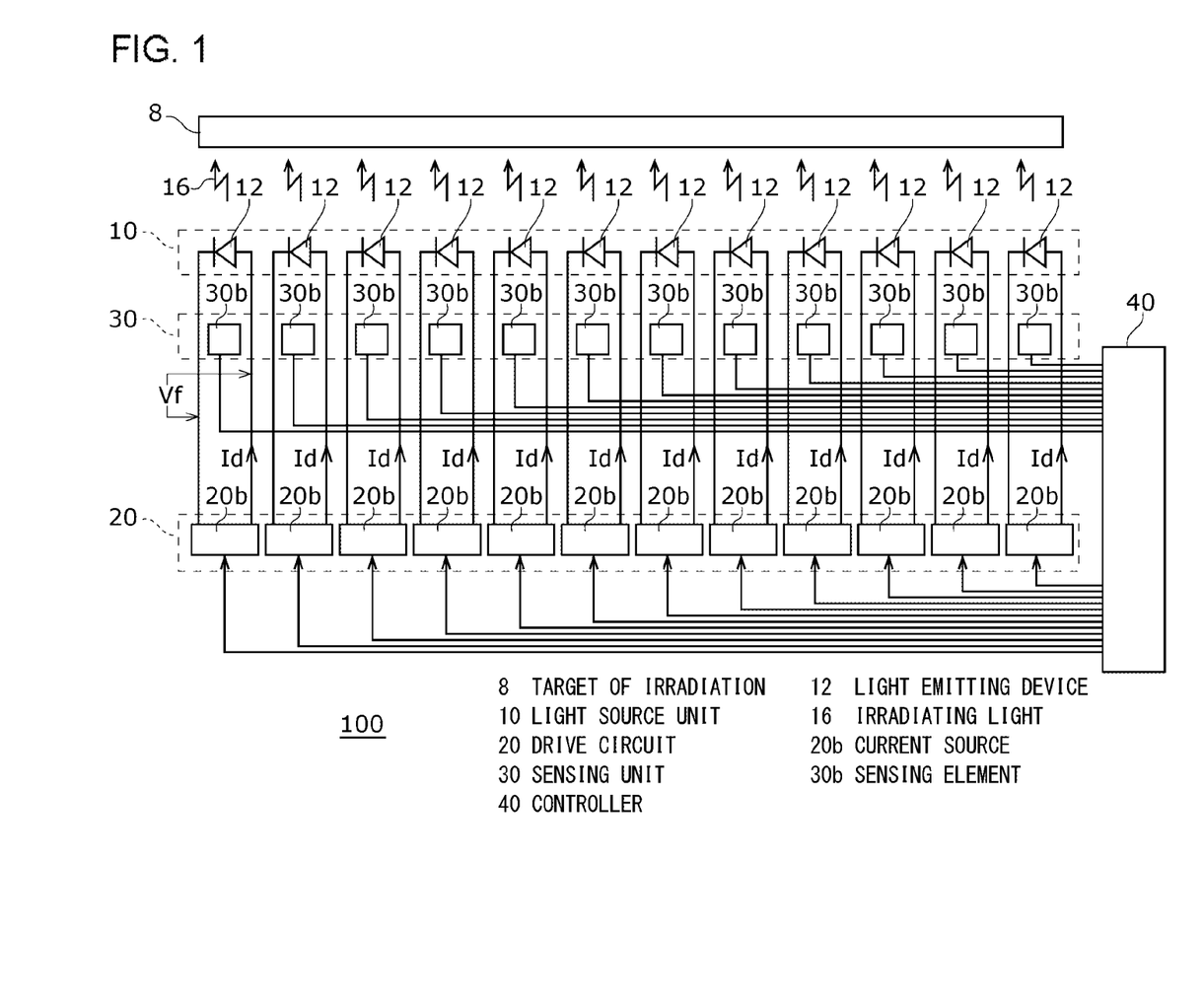
FIG. 1 is a block diagram schematically showing a configuration of the irradiation device according to the first embodiment.
Figure 2:
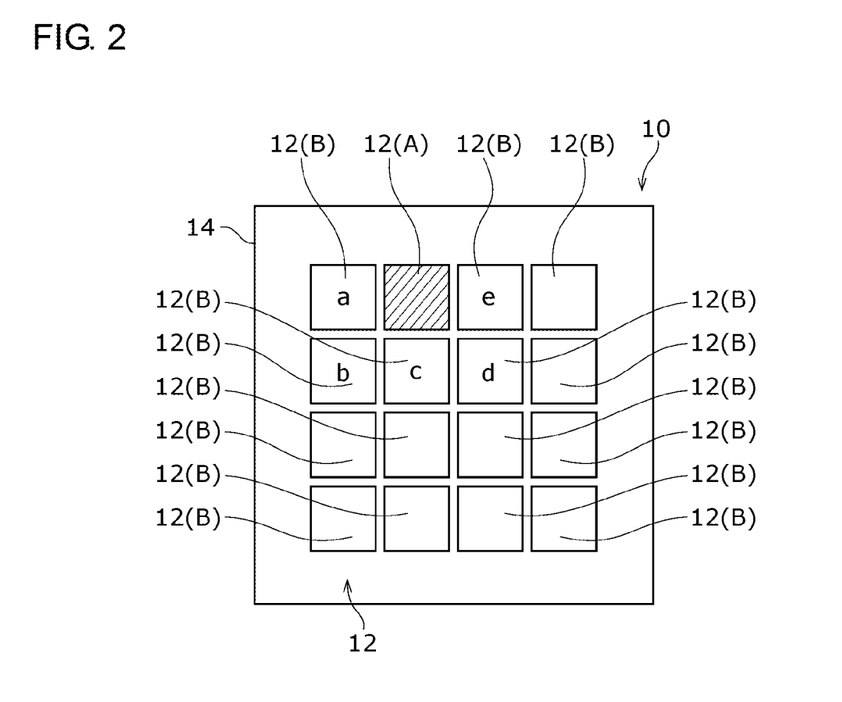
FIG. 2 schematically shows an exemplary arrangement of light emitting devices of the irradiation device of FIG. 1.

A description will now be given of an irradiation device 100 according to a first embodiment of the present invention with reference to the drawings. FIG. 1 is a block diagram schematically showing a configuration of the irradiation device 100 according to the first embodiment. FIG. 2 schematically shows an exemplary arrangement of a plurality of light emitting devices 12 of a light source unit 10. The irradiation device 100 functions as an ultraviolet irradiation device configured to output ultraviolet light as irradiating light 16 to a target of irradiation 8. The irradiation device 100 mainly includes a light source unit 10, a drive circuit 20, a sensing unit 30, and a controller 40.

The target of irradiation 8 could be anything so long as it is adapted to be irradiated with ultraviolet light. The target of irradiation 8 may be a solid, gel, liquid, gas, or a combination thereof. The irradiating light 16 could be any ultraviolet light having wavelength characteristics that affect the target of irradiation 8 in some way. Known functions of the irradiating light 16 include sterilization, surface treatment, reaction treatment, etc.

(Light Source Unit)

The light source unit 10 includes the plurality of light emitting devices 12 and outputs ultraviolet light as the irradiating light 16. The light source unit 10 includes a substrate 14 and the plurality of light emitting devices 12 provided on the substrate 14. Any of various publicly known substrates can be employed for the substrate 14. The plurality of light emitting devices 12 may be arranged on a plane in a matrix of N rows and M columns (N and M are integers equal to or larger than 2). N and M may be identical or different. N and M can be defined to suit the desired illuminance and desired wavelength characteristics. In the example of FIG. 2, 16 light emitting devices 12 are arranged in an array of 4 rows and 4 columns.

By way of example, the plurality of light emitting devices 12 may output the irradiating light 16 of wavelength characteristics having a function of killing microbes. The plurality of light emitting devices 12 may output light of a single wavelength or output light of a plurality of wavelengths. In this example, the plurality of light emitting devices 12 are light emitting diodes (LEDs) configured to emit ultraviolet light, and the central wavelength or peak wavelength thereof is included in a range of about 200 nm~350 nm. It is preferable that the plurality of light emitting devices 12 emit ultraviolet light near a wavelength range of 260 nm~290 nm having a high sterilizing efficiency. Such an ultraviolet LED is exemplified by an aluminum gallium nitride (AlGaN) based LED.

(Drive Circuit)

The drive circuit 20 supplies a drive current Id to each of the plurality of light emitting devices 12. The drive circuit 20 may include a plurality of current sources 20b respectively corresponding to the plurality of light emitting devices 12. In the example of FIG. 2, the drive circuit 20 includes 16 current sources 20b respectively corresponding to the 16 light emitting devices 12. The current source 20b could be anything so long as it is capable of supplying the drive current Id to the light emitting device 12. By way of example, the current source 20b may be a publicly known current source such as a constant-current circuit or a circuit including a combination of series resistors and a voltage source.

(Sensing Unit)

The sensing unit 30 senses a trouble in each of the plurality of light emitting devices 12. The sensing unit 30 may include a plurality of sensing elements 30b respectively corresponding to the plurality of light emitting devices 12. In the example of FIG. 2, the sensing unit 30 includes 16 sensing elements 30b respectively corresponding to the 16 light emitting devices 12. The sensing element 30b could be anything so long as it is capable of sensing a state in which the light emitting device 12 is in trouble. A state in which the light emitting device 12 is in trouble may include a state in which the light emitting function of the light emitting device 12 is lost in part or in its entirety. A trouble or a failure in the light emitting device 12 may be caused by a trouble such as disconnection, short circuit, and the degradation of junctions.

A description will be given of exemplary principles for sensing a state in which the light emitting device 12 is in trouble. (1) The sensing unit 30 may be configured to sense a trouble in each light emitting device 12 in accordance with one of the drive current Id and a forward voltage Vf of each light emitting device 12. For example, the sensing element 30b may detect, as a detection value, at least one of the drive current Id and the forward voltage Vf of the light emitting device 12. The sensing element 30b may sense that the light emitting device 12 is in trouble when the detection value is outside a preset range.

Where the light emitting device 12 is an LED drive by a constant current, for example, the sensing element 30b may sense that there is an electrically open failure in the LED if the forward voltage Vf of the LED is larger than the preset range. Further, the sensing element 30b may sense a short circuit failure in the LED if the forward voltage Vf is smaller than the preset range. Still further, the sensing element 30b may sense that there is an electrically open failure in the LED if the forward current of the LED is smaller than the preset range. The preset ranges of the forward voltage Vf and the forward current may be set based on the voltage-current characteristics of the LED.

(2) The sensing unit 30 may be configured to sense a trouble in the light emitting device 12 in accordance with the temperature of the substrate 14 carrying the light emitting device 12. For example, the sensing element 30b may include a temperature sensing element provided near the light emitting device 12 on the substrate 14. The temperature sensing element could be any element so long as it is capable of detecting the temperature of the substrate 14. The temperature sensing element may include a publicly known temperature sensing device such as a thermistor. For example, the sensing element 30b may include a thermistor provided near the light emitting device 12. In this case, the sensing element 30b can sense that the light emitting device 12 is in trouble if the resistance of the thermistor is outside a preset range.

For example, when the light emitting device 12 is in trouble, an temperature increase due to power consumption does not occur so that the temperature of the substrate carrying that light emitting device 12 is lower than that of the other substrates. Accordingly, the sensing element 30b can sense that the light emitting device 12 is in trouble if the resistance of the thermistor (e.g., NTC thermistor) is larger than a threshold value. The substrate 14 may be divided to carry the respective light emitting devices 12 in order to reduce the impact from heat dissipation in other light emitting devices 12. The preset range of the resistance of the thermistor may be set based on the characteristics of the resistance of the thermistor with respect to the temperature.

(3) The sensing unit 30 may be configured to sense a trouble in each light emitting device 12 in accordance with the illuminance of the light emitted by each light emitting device 12. For example, the sensing element 30b may include an illuminance detecting element for detecting the illuminance of light emitted by the light emitting device 12. The illuminance detecting element could be any element so long as it is capable of detecting the illuminance of light emitted by the light emitting device 12. The illuminance detecting element may include a publicly known sensing device such as a photodiode (PD). For example, the sensing element 30b may include a PD located at a position where it is capable of receiving the light emitted by the light emitting device 12. In this case, the sensing element 30b can sense that the light emitting device 12 is in trouble if the photo current of the PD is outside a preset range.

If the light emitting device 12 is in trouble and does not emit light, the photo current of the PD corresponding to that light emitting device is smaller than that of the PDs corresponding to the other light emitting devices. Therefore, when the photo current of a PD is smaller than a threshold value, the sensing element 30b can sense that the corresponding light emitting device 12 is in trouble. The preset range of the photo current of the PD may be set based on the characteristics of the photo current with respect to the input illuminance of the PD.

(Controller)

The controller 40 controls the drive current Id in accordance with a result of sensing by the sensing unit 30. The controller 40 may be implemented by a publicly known central processing unit (CPU) or the like. If one or some of the plurality of light emitting devices 12 (hereinafter, referred to as a light emitting device 12(A)) is in trouble, the light source unit 10 outputs the irradiating light 16 from the normal light emitting devices (hereinafter, light emitting devices 12(B)) other than the light emitting device 12(A). In this case, the number of light emitting devices that emit light is reduced and the output of the light source unit 10 is reduced accordingly. Thus, when the output of the light source unit 10 is reduced due to a trouble in one or some of the plurality of light emitting devices 12, the controller 40 according to the first embodiment controls the drive current Id of the plurality of light emitting devices 12(B) other than the light emitting device 12(A) in trouble to correct the output of the light source unit 10. Stated otherwise, when the output of the light source unit 10 changes due to a trouble in one or some of the light emitting devices, the controller 40 controls the drive current Id so as to cancel the change in the output.

For example, in the event of a trouble in Q (Q is an integer equal to or greater than 1 and smaller than P) light emitting devices 12 in the light source unit 10 provided with P (P is an integer equal to or greater than 2), the controller 40 may control the drive circuit 20 to increase the drive current Id in accordance with P and Q. In this case, the controller 40 may, for example, multiply the drive current Id by P/(P−Q) times for correction. Given that P=16 and Q=1, the drive current Id may, for example, be increased by 1.067 times.

Figure 3:
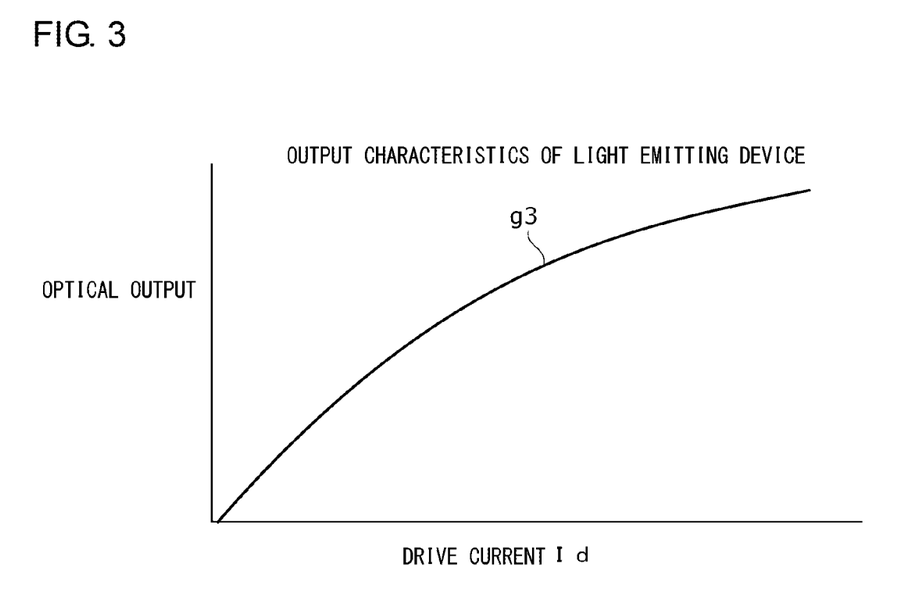
FIG. 3 is a graph schematically showing output characteristics of the light emitting device of the irradiation device of FIG. 1.

If the output characteristics of the light emitting device 12 is nonlinear, it is desired to correct the drive current Id by allowing for the output characteristics of the light emitting device 12. FIG. 3 is a graph schematically showing exemplary output characteristics g3 of the light emitting device 12 of the irradiation device 100. Referring to FIG. 3, the horizontal axis represents the drive current Id of the light emitting device 12, and the vertical axis represents the optical output of the light emitting device 12. As shown in FIG. 3, the optical output of the light emitting device 12 may vary nonlinearly with respect to the drive current Id. In this case, the optical output will be insufficient by correcting the drive current Id as described above.

To address this issue, the controller 40 according to the first embodiment is provided with an optical output relationship table showing the relationship of the optical output with respect to the drive current Id of the light emitting device 12. The controller 40 calculates the optical output that should result from the correction in accordance with P and Q and acquires a correction value of the drive current Id from the optical output relationship table based on the calculated optical output. The controller 40 controls the drive circuit 20 so as to induce the drive current Id based on the correction value acquired. The irradiation device 100 compensates the shortage of optical output by exercising the above control.

Figure 4:
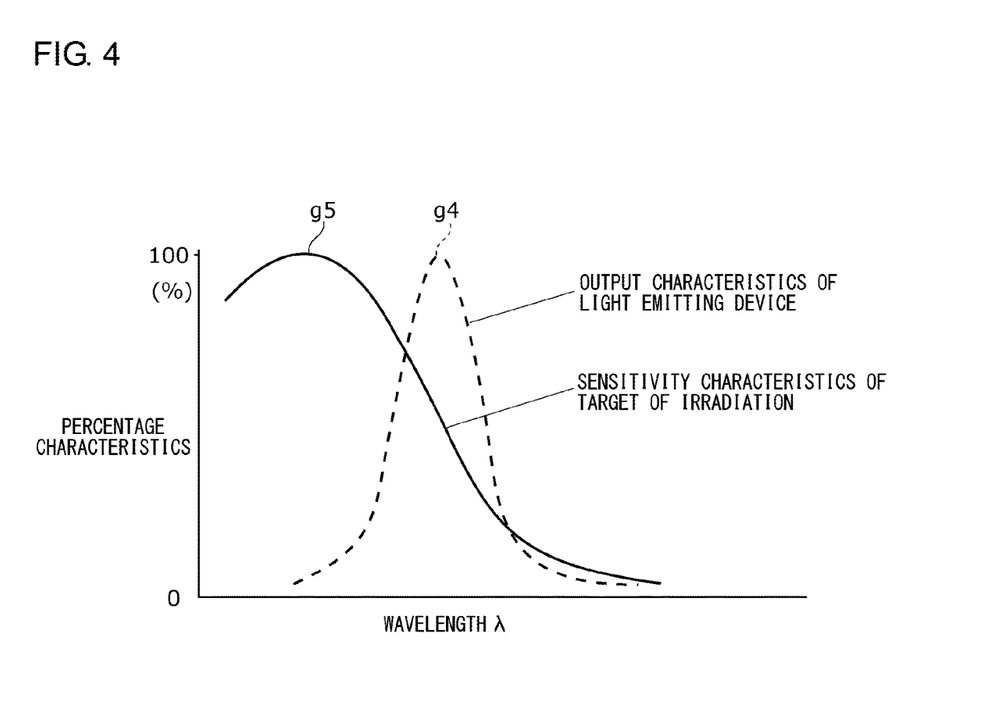
FIG. 4 is a graph schematically showing an exemplary relationship between wavelength characteristics of the light emitting device and the sensitivity characteristics of the target of irradiation of FIG. 1.

If the plurality of light emitting devices 12 include light emitting devices that differ in the wavelength characteristics, it is desired to correct the drive current Id by allowing for the relationship between the wavelength characteristics of the light emitting device 12 and the sensitivity characteristics of the target of irradiation 8. FIG. 4 is a graph schematically showing an exemplary relationship between the wavelength characteristics g4 of the light emitting device 12 and the sensitivity characteristics of the target of irradiation 8. Referring to FIG. 4, the horizontal axis represents the wavelength A, and the vertical axis represents the wavelength characteristics of the light emitting device 12 and the sensitivity characteristics of the target of irradiation 8. FIG. 4 shows the percentage characteristics, the peak characteristics being defined as 100%. The performance of the irradiating light 16 to affect the target of irradiation 8 is considered to be proportional to a value obtained by integrating a product of the wavelength characteristics g4 and the sensitivity characteristics g5 over a predetermined range of wavelength.

To address this, the controller 40 according to the first embodiment is provided with a wavelength/sensitivity characteristics relationship table showing the relationship of the wavelength characteristics g4 of the light emitting devices 12 and the sensitivity characteristics g5 of the target of irradiation 8 with respect to the wavelength A. The controller 40 calculates an amount by which the performance of the irradiating light 16 should be corrected in accordance with P and Q. The controller 40 refers to the wavelength/sensitivity characteristics relationship table based on the calculated amount of correction of the performance so as to acquire the optical output that should result from the correction and identifies the correction amount of the drive current Id from the optical output relationship table based on the acquired optical output. The controller 40 controls the drive circuit 20 so as to induce the drive current Id based on the identified correction value. The irradiation device 100 compensates the shortage of the optical output and the performance by exercising the above control.

If the plurality of light emitting devices 12 include light emitting devices that differ in the wavelength characteristics, it is desired to correct the drive current Id by allowing for a change in the wavelength characteristics. Thus, if the wavelength characteristics of the irradiating light 16 changes due to a trouble in one or some of the plurality of light emitting devices 12, the controller 40 of the irradiation device 100 according to the first embodiment controls the drive current Id of the light emitting devices 12 so as to cancel the change in the wavelength characteristics.

If the plurality of light emitting devices 12 are provided on a plane, it is desired to correct the drive current Id by allowing for the position where the light emitting device 12(A) in trouble is provided. If the plurality of light emitting devices 12 are arranged in a matrix as shown in FIG. 2, the light source unit 10 has a certain illuminance distribution. By way of example, if the light emitting device 12(A) shown in FIG. 2 is in trouble, the illuminance of irradiated region corresponding to the light emitting device 12(A) becomes lower than that of the other irradiated regions. In this state, the illuminance distribution of the light source unit 10 is deviated from the predetermined illuminance distribution. If the drive current Id is corrected by the same rate for all of the remaining light emitting devices 12(B) while the illuminance distribution remains deviated from the original, the optical output as a whole will be corrected but deviation in the illuminance distribution remains. In other words, the irradiated region corresponding to the light emitting device 12(A) in trouble remains relatively darker than the other irradiated regions.

Thus, if the illuminance distribution of the irradiating light 16 changes due to a trouble in one or some of the plurality of light emitting devices 12, the controller 40 according to the first embodiment controls the drive current Id of the light emitting devices 12 so as to cancel the change in the illuminance distribution. By way of example, if the light emitting device 12(A) shown in FIG. 2 is in trouble, the correction amount of the drive current Id for the three (a, c, d in FIG. 2) or 5 (a~d in FIG. 2) light emitting devices 12(B) surrounding the light emitting device 12(A) may be configured to be larger than the correction amount of the drive current Id for the other light emitting devices 12(B).

The controller 40 is provided with a coefficient relationship table showing, for each of the light emitting devices 12 listed, a coefficient for correcting the drive current Id for the other light emitting devices 12 in the event of a trouble in the listed light emitting device 12. The controller 40 refers to the coefficient relationship table based on the position of the light emitting device 12(A) in trouble to acquire the correction coefficient for the each of the other light emitting devices 12(B). The controller 40 controls the drive circuit 20 to induce the drive current Id based on the correction coefficient acquired. The irradiation device 100 operates to cancel the changed in the illuminance distribution by exercising the above control.

If one or some of the plurality of light emitting devices 12 is in trouble and the light emitting device 12(A) in trouble continues to be energized, the drive current Id for the other normal light emitting devices 12(B) may become insufficient. The controller 40 according to the first embodiment addresses this issue by controlling the drive circuit 20 to stop energizing the light emitting device 12(A) in trouble when the sensing unit 30 senses a trouble. This reduces the likelihood that the drive current If for the normal light emitting devices 12(B) becomes insufficient.

When the drive current Id exceeding the permitted current or the permitted power is supplied to the light emitting device 12, the degradation of that light emitting device 12 is accelerated, and a trouble may be caused. The controller 40 according to the first embodiment addresses this issue by controlling the drive circuit 20 to supply the drive current Id such that the permitted current or the permitted power is not exceeded. In this case, the degradation of the light emitting device 12 is inhibited.

If the junction temperature of the light emitting device 12 exceeds the permitted range, the degradation of the light emitting device 12 is accelerated, and a trouble may be caused. The controller 40 according to the first embodiment addresses this issue by controlling the drive circuit 20 to supply the drive current Id in a range in which the junction temperature does not exceed the permitted range. The irradiation device 100 may be provided with a sensing means for sensing the substrate temperature. The junction temperature is identified by computation that uses the internal power loss of the light emitting device 12 and the substrate temperature as parameters. The internal power loss is calculated as a product of the forward voltage Vf and the drive current Id. The controller 40 can identify the junction temperature of the light emitting device 12 based on the substrate temperature, the forward voltage Vf, and the drive current Id. The controller 40 can control the drive current Id in a range in which the junction temperature identified does not exceed the permitted range. In this case, the degradation of the light emitting device 12 is inhibited.

A description will now be given of the function and advantage of the irradiation device 100 according to the first embodiment configured as described above.

The irradiation device 100 according to the first embodiment includes: a plurality of light emitting devices 12; a light source unit 10 that outputs ultraviolet light as irradiating light 16; a drive circuit 20 that supplies a drive current Id to the plurality of light emitting devices 12; a sensing unit 30 that senses a trouble in the plurality of light emitting devices 12; and a controller 40 that controls the drive current Id in accordance with a result of sensing by the sensing unit 30, wherein, when the output of the light source unit 10 is reduced due to a trouble in one or some of the plurality of light emitting devices 12, the controller 40 controls the drive current Id of a plurality of light emitting devices 12 other than the light emitting devices 12 in trouble so as to compensate the reduction in the output of the light source unit 10. According to this configuration, the output of the light source unit 10 can be corrected by controlling the drive current Id of light emitting devices 12(B) other than the light emitting device 12(A) in trouble. This inhibits reduction in the performance (e.g., sterilization performance) of the irradiation device 100 as compared with the case where the output of the light source unit is not corrected.

In the irradiation device 100 according to the first embodiment, the sensing unit 30 is configured to sense a trouble in each light emitting device 12 in accordance with at least one of the drive current Id and the forward voltage Vf of each light emitting device 12. According to this configuration, a trouble in the light emitting device 12 is sensed in a simplified manner and properly by monitoring the drive current Id or the forward voltage Vf of the light emitting device 12 with reference to a predetermined range.

In the irradiation device 100 according to the first embodiment, the sensing unit 30 is configured to sense a trouble in each light emitting device 12 in accordance with the temperature of the substrate on which each light emitting device 12 is mounted. According to this configuration, a trouble in the light emitting device 12 is sensed properly by monitoring the relationship between the drive current Id of the light emitting device 12 and the temperature of the light emitting device 12 dissipating heat with reference to a predetermined range.

In the irradiation device 100 according to the first embodiment, the sensing unit 30 is configured to sense a trouble in each light emitting device 12 in accordance with the illuminance of light emitted by each light emitting device 12. According to this configuration, a trouble in the light emitting device 12 is sensed properly by monitoring the illuminance of light emitted by the light emitting device 12 with reference to a predetermined range.

In the irradiation device 100 according to the first embodiment, the controller 40 controls, when the illuminance distribution of the irradiating light 16 changes due to a trouble in one or some of the plurality of light emitting devices 12, the drive current Id of each light emitting device 12 so as to cancel changed in the illuminance distribution. According to this configuration, control is exercised so as to cancel the changed in the illuminance distribution. Therefore, unevenness in the illuminance distribution is inhibited as compared with the case of simply controlling the drive current Id.

In the irradiation device 100 according to the first embodiment, the controller 40 controls, when the wavelength characteristics of the irradiating light 16 change due to a trouble in one or some of the plurality of light emitting devices 12, the drive current Id of each light emitting device 12 so as to cancel change in the wavelength characteristics. According to this configuration, control is exercised so as to cancel the change in the wavelength characteristics. Therefore, the change in the wavelength characteristics is inhibited as compared with the case of simply controlling the drive current Id.

Second Embodiment

Figure 5:
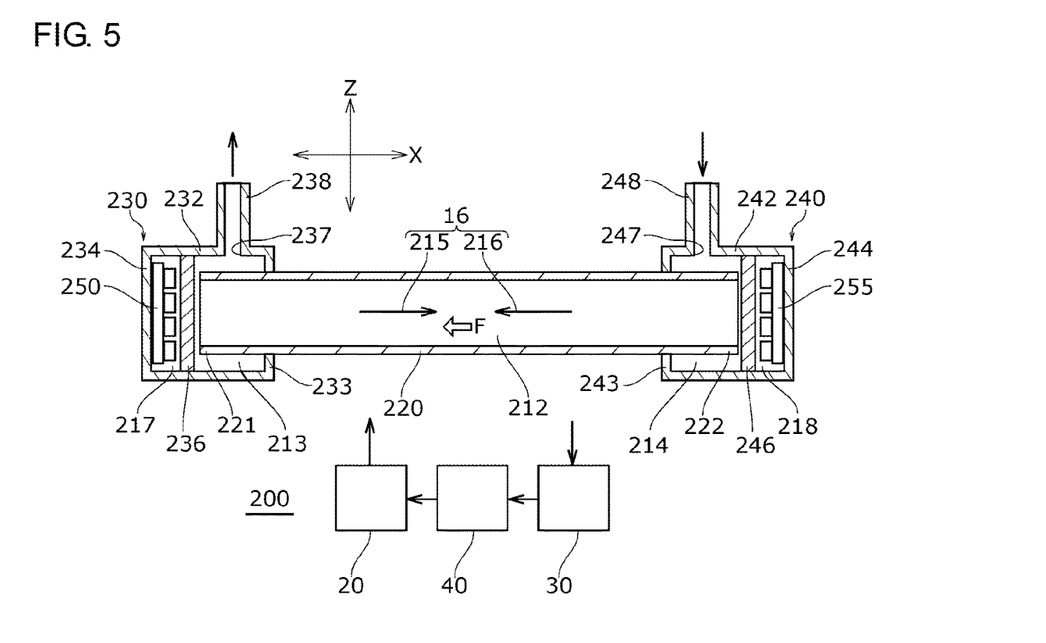
FIG. 5 is a cross-sectional view schematically showing a configuration of an irradiation device according to the second embodiment.
Figure 6A:
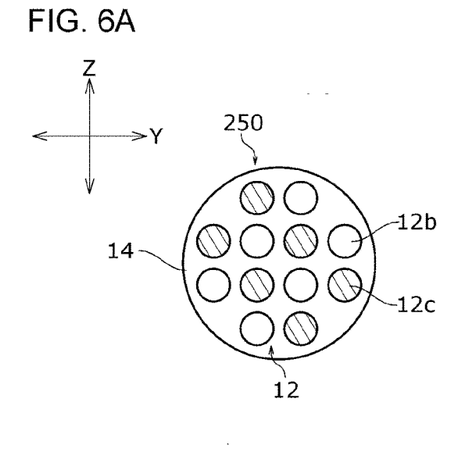
FIG. 6A schematically shows an exemplary arrangement of the light emitting devices of the irradiation device of FIG. 5.
Figure 6B:
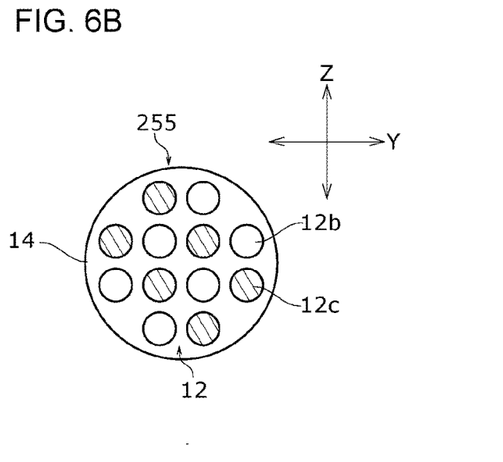
FIG. 6B schematically shows an alternative exemplary arrangement of the light emitting devices of the irradiation device of FIG. 5.

A description will now be given of an irradiation device 200 according to a second embodiment of the present invention with reference to FIG. 5, FIG. 6A, and FIG. 6B. In the drawings and description of the second embodiment, constituting elements and members identical or equivalent to those of the first embodiment shall be denoted by the same reference numerals. Duplicative explanations are omitted appropriately and features different from those of the first embodiment will be highlighted. FIG. 5 is a cross-sectional view schematically showing a configuration of the irradiation device 200 according to the second embodiment. FIG. 6A schematically shows an exemplary arrangement of the light emitting devices 12 of the irradiation device 200. FIG. 6B schematically shows an alternative exemplary arrangement of the light emitting devices 12 of the irradiation device 200.

The description below is based on an XYZ coordinate system. The X-axis direction corresponds to the horizontal direction on the plane of paper in FIG. 5 and corresponds to the direction perpendicular to the plane of paper in FIG. 6A and FIG. 6B. The Y-axis direction corresponds to the direction perpendicular to the plane of paper in FIG. 5 and corresponds to the horizontal direction on the plane of paper in FIG. 6A and FIG. 6B. The Z-axis direction corresponds to the vertical direction on the plane of paper in FIG. 5, FIG. 6A, and FIG. 6B. The Y-axis direction and the Z-axis direction are perpendicular to the X-axis direction. The notation of directions above shall not limit the orientation of the irradiation device 200 in use, and the irradiation device 200 may be used in any orientation.

The irradiation device 200 mainly include a flow passage tube 220, a first housing 230, a second housing 240, a first light source unit 250, a second light source unit 255, the drive circuit 20, the sensing unit 30, and the controller 40. The first light source unit 250 and the second light source unit 255 irradiate the interior of the flow passage tube 220 with ultraviolet light as irradiating light 215, 216. The irradiation device 200 functions as a fluid sterilization device for sterilizing a fluid (water etc.) flowing inside the flow passage tube 220 by irradiating the fluid with ultraviolet light.

The drive circuit 20 of the irradiation device 200 supplies the drive current Id to the plurality of light emitting devices 12 of the first light source unit 250 and the second light source unit 255. The sensing unit 30 of the irradiation device 200 senses a trouble in the plurality of light emitting devices 12 of the first light source unit 250 and the second light source unit 255. When the output of the first light source unit 250 or the second light source unit 255 is reduced due to a trouble in one or some of the plurality of light emitting devices 12 in these light source units, the controller 40 of the irradiation device 200 controls the drive current Id of a plurality of light emitting devices 12 other than the light emitting device in trouble so as to compensate the reduction in the output of these light source units. The configuration and feature of the drive circuit 20, the sensing unit 30, and the controller 40 of the irradiation device 200 are similar to the drive circuit 20, the sensing unit 30, and the controller 40 according to the first embodiment and the description above is applicable.

The flow passage tube 220 is a hollow cylindrical straight tube extending in the X-axis direction. The flow passage tube 220 has a first end 221 and a second end 222 opposite to the first end 221. A fluid flows from the second end 222 toward the first end 221 in a direction indicated by an arrow F. The first irradiating light 215 from the first light source unit 250 is incident on the first end 221 and the second irradiating light 216 from the second light source unit 255 is incident on the second end 222. The flow passage tube 220 defines a processing passage 212 in which the fluid is irradiated with ultraviolet light.

The flow passage tube 220 is made of a metal material or a resin material. The flow passage tube 220 is desirably made of a material having a high ultraviolet reflectivity. For example, the inner surface of the flow passage tube 220 is made of mirror-polished aluminum (Al) or polytetrafluoroethylene (PTFE), which is a fully fluorinated resin. By forming the flow passage tube 220 using a material like the above, the first irradiating light 215, 216 emitted by the first light source unit 250 and the second light source unit 255 can be reflected to propagate in the longitudinal direction of the flow passage tube 220. In particular, PTFE is a chemically stable material and has a high ultraviolet reflectivity and so is suitable as the material for the flow passage tube 220 forming the processing passage 212.

A description will now be given of the first housing 230. In the description of the first housing 230, the direction toward the second end 222 in the X-axis direction will be referred to as an inner/inward, and the direction away from the second end 222 in the X-axis direction will be referred to as outer/outward. The first housing 230 is provided to encircle the first end 221. The first housing 230 defines a first straightening chamber 213 and a first light source chamber 217. The first housing 230 is made of a metal material or a resin material. It is desired that the first housing 230 be made of a material having a low reflectivity for the ultraviolet light emitted by the first light source unit 250 and be made of a material having a lower ultraviolet reflectivity than the flow passage tube 220. The first housing 230 may be made of a material that absorbs the ultraviolet light from the first light source unit 250. By configuring the first housing 230 by using a material like the above, the ultraviolet light from the first light source unit 250 is inhibited from being reflected by the inner surface of the first housing 230 and leaking outside via an outflow tube 238.

The first housing 230 has a first side wall 232, a first inner end wall 233, and a first outer end wall 234. The first side wall 232 is a hollow cylindrical member extending from the first inner end wall 233 to the first outer end wall 234 in the X-axis direction and is provided at a position substantially coaxial with the flow passage tube 220. The first inner end wall 233 is a member extending radially outward from the side wall of the flow passage tube 220 to the first side wall 232 and has an annular shape (doughnut shape). The first inner end wall 233 is provided at a position inward from the first end 221 in the X-axis direction and is fixed to the outer surface of the flow passage tube 220. The first outer end wall 234 is a disc-shaped member provided at a position outward from the first end 221 in the X-axis direction. Therefore, the first inner end wall 233 and the first outer end wall 234 are provided at positions opposite to each other in the X-axis direction, sandwiching the first end 221.

A first window 236 for transmitting the first irradiating light 215 from the first light source unit 250 is provided inside the first housing 230. The first window 236 is made of a material having a high ultraviolet transmittance such as quartz (SiO2), sapphire (Al2O3), and amorphous fluororesin. The first window 236 partitions the interior of the first housing 230 into the first straightening chamber 213 and the first light source chamber 217. The first straightening chamber 213 is an area defined by the first side wall 232, the first inner end wall 233, and the first window 236 and is an area provided annularly to encircle the first end 221 from outside in the radial direction. The first light source chamber 217 is an area defined by the first side wall 232, the first outer end wall 234, and the first window 236 and is provided with the first light source unit 250.

The first window 236 is a facing member that faces the first end 221 in the X-axis direction and is provided in the vicinity of the first end 221 so as to provide a small gap relative to the first end 221. The first housing 230 is provided with an outflow port 237 and an outflow tube 238. The outflow port 37 is a communication port through which the fluid irradiated with irradiating light in the processing passage 212 flows out and is provided at a position communicating with the first straightening chamber 213. For example, the outflow port 237 is provided in the first side wall 232 as illustrated. The outflow tube 238 is a connecting pipe fitted to the outflow port 237 and is configured such that a pipe or a tube connector for connection to the irradiation device 200 can be mounted.

The first light source unit 250 is provided inside the first light source chamber 217 and is arranged to output the first irradiating light 215 toward the opening of the first end 221. The first light source unit 250 includes the substrate 14 and the plurality of light emitting devices 12 arranged on the substrate. The plurality of light emitting devices 12 are fitted to the substrate 14 so as to face the first window 236. The substrate 14 is made by using a highly exoergic member, and copper (Cu), aluminum (Al), or the like is used as a base material. The heat generated by the light emitting device 12 is dissipated via the substrate 14.

A description will now be given of the second housing 240. In the description of the second housing 240, the direction toward the first end 221 in the X-axis direction will be referred to as an inner/inward, and the direction away from the first end 221 in the X-axis direction will be referred to as outer/outward. The second housing 240 is configured in a manner similar to that of the first housing 230. The second housing 240 is provided to encircle the second end 222. The second housing 240 defines a second straightening chamber 214 and a second light source chamber 218. The second housing 240 has a second side wall 242, a second inner end wall 243, and a second outer end wall 244.

The second side wall 242 is a hollow cylindrical member extending from the second inner end wall 243 to the second outer end wall 244 in the X-axis direction. The second side wall 242 is provided at a position substantially coaxial with the flow passage tube 220. The second inner end wall 243 is an annular member provided at a position inward from the second end 222 in the X-axis direction and is fixed to the outer surface of the flow passage tube 220. The second outer end wall 244 is a disc-shaped member provided at a position outward from the second end 222 in the X-axis direction. The second inner end wall 243 and the second outer end wall 244 are provided at positions opposite to each other in the X-axis direction, sandwiching the second end 222.

A second window 246 for transmitting the second irradiating light 216 from the second light source unit 255 is provided inside the second housing 240. The second window 246 partitions the interior of the second housing 240 into the second straightening chamber 214 and the second light source chamber 218. The second straightening chamber 214 is an area defined by the second side wall 242, the second inner end wall 243, and the second window 246 and is an area provided annularly to encircle the second end 222 from outside in the radial direction. The second light source chamber 218 is an area defined by the second side wall 242, the second outer end wall 244, and the second window 246 and is provided with the second light source unit 255.

The second window 246 is a facing member that faces the second end 222 in the X-axis direction. The second window 246 is provided in the vicinity of the second end 222 so as to provide a gap relative to the second end 222. It is preferable that the end face of the second end 222 and the surface of the second window 246 facing the second end 222 be substantially parallel.

The second housing 240 is provided with an inflow tube 248 and an inflow port 247. The inflow port 247 is a communication port for the fluid flowing into the processing passage 212 and is provided at a position communicating with the second straightening chamber 214. The inflow tube 248 is is a connecting pipe fitted to the inflow port 247.

The second light source unit 255 is provided inside the second light source chamber 218 and is arranged to output the second irradiating light 216 toward the second end 222. As in the case of the first light source unit 250, the second light source unit 255 is provided in the vicinity of the second end 222. As shown in FIG. 6A and FIG. 6B, the second light source unit 255 is configured in a manner similar to that of the first light source unit 250.

With the above-described configuration, the irradiation device 200 irradiates the fluid flowing in the processing passage 212 with the first irradiating light 215 from the first light source unit 250 and the second irradiating light 216 from the second light source unit 255 so as to sterilize the fluid. The fluid subject to the treatment flows into the processing passage 212 via the inflow tube 248, the inflow port 247, the second straightening chamber 214, and the second end 222. The fluid passing through the processing passage 212 flows out from the first end 221 via the first straightening chamber 213, the outflow port 237, and the outflow tube 238.

The light source unit may include light emitting devices having different wavelength characteristics. In the example of FIG. 6A and FIG. 6B, the first light source unit 250 and the second light source unit 255 include light emitting devices 12b and 12c that emit ultraviolet light having different wavelength characteristics. The light emitting devices 12b and 12c are alternately arranged in the Z-axis direction and the Y-axis direction. When the wavelength characteristics of the irradiating light 215 or the irradiating light 216 changes due to a trouble in one or some of the plurality of light emitting devices 12 in the first light source unit 250 or the second light source unit 255, the controller 40 of the irradiation device 200 controls the drive current Id of the light emitting devices 12 to cancel the change in the wavelength characteristics.

A description will now be given of the operation of the controller 40 of the irradiating device 200 according to the second embodiment. The controller 40 of the irradiation device 200 can perform an operation similar to the control operation described in the first embodiment. In addition, the controller 40 of the irradiation device 200 can exercise control described below.

The first light source unit 250 and the second light source unit 255 output the first irradiating light 215 and the second irradiating light 216 from mutually different positions and in mutually different directions toward the fluid subject to the treatment. In other words, the fluid subject to irradiation is irradiated with irradiating light including the first irradiating light 215 and the second irradiating light 216 output from mutually different positions and in mutually different directions. The first irradiating light 215 radiated from the fluid exit side (the side of the first end 221) in the processing passage 212 and the second irradiating light 216 radiated from the entrance side (the side of the second end 222) may differ in the sterilization effect.

For this reason, a predetermined output ratio (output balance) may be defined for the outputs of the first irradiating light 215 and the second irradiating light 216 in order to optimize the sterilization effect of the irradiation device 200 as a whole. Optimization of the sterilization effect includes minimizing the total drive current to obtain a desired sterilization effect and maximizing the sterilization effect under a certain total drive current. Even if the output balance is lost, the output balance is corrected based on the contribution of the light sources in the respective directions of irradiation. Therefore, the output ratio may change so long as ultraviolet light necessary for sterilization can be radiated.

Thus, when the output ratio between the first irradiating light 215 and the second irradiating light 216 changes due to a trouble in one or some of the plurality of light emitting devices 12, the controller 40 according to the second embodiment controls the drive current Id of the light emitting devices 12 so as to cancel the change in the output ratio. By way of example, the output of the first irradiating light 215 is reduced and the output of the second irradiating light 216 does not change when the light emitting device 12 in the first light source unit 250 is in trouble. Therefore, the output ratio of the second irradiating light 216 relative to the first irradiating light 215 changes in the increasing direction. In this case, the drive current Id of the light emitting device 12 in the first light source unit 250 may be corrected more than the drive current Id of the light emitting device 12 of the second light source unit 255 so as to cancel the change in the output ratio.

The irradiation device 200 according to the second embodiment provides the function and advantage similar to those of the irradiation device 100 according to the first embodiment. In addition, the second irradiation device 200 according to the second embodiment provides the following function and advantage.

In the irradiation device 200 according to the second embodiment, the irradiating light 16 includes the first irradiating light 215 and the second irradiating light 216 output in mutually different directions. When the output ratio between the first irradiating light 215 and the second irradiating light 216 changes due to a trouble in one or some of the plurality of light emitting devices 12, the controller 40 controls the drive current Id of the light emitting devices 12 so as to cancel the change in the output ratio. According to this configuration, control is exercised so as to cancel the change in the output ratio. Therefore, the change in output ratio is inhibited as compared with the case of simply controlling the drive current Id. This reduces the change in the sterilization effect provided by the irradiation device 200.

Described above is an explanation based on an exemplary embodiment. The embodiments are intended to be illustrative only and it will be understood to those skilled in the art that variations and modifications are possible within the claim scope of the present invention and that such variations and modifications are also within the claim scope of the present invention. Therefore, the description in this specification and the drawings shall be treated to serve illustrative purposes and shall not limit the scope of the invention.

A description will now be given of variations. In the drawings and description of the variations, constituting elements and members identical or equivalent to those of the embodiments shall be denoted by the same reference numerals. Duplicative explanations are omitted appropriately and features different from those of the first embodiment will be highlighted.

(First Variation)

Figure 7:
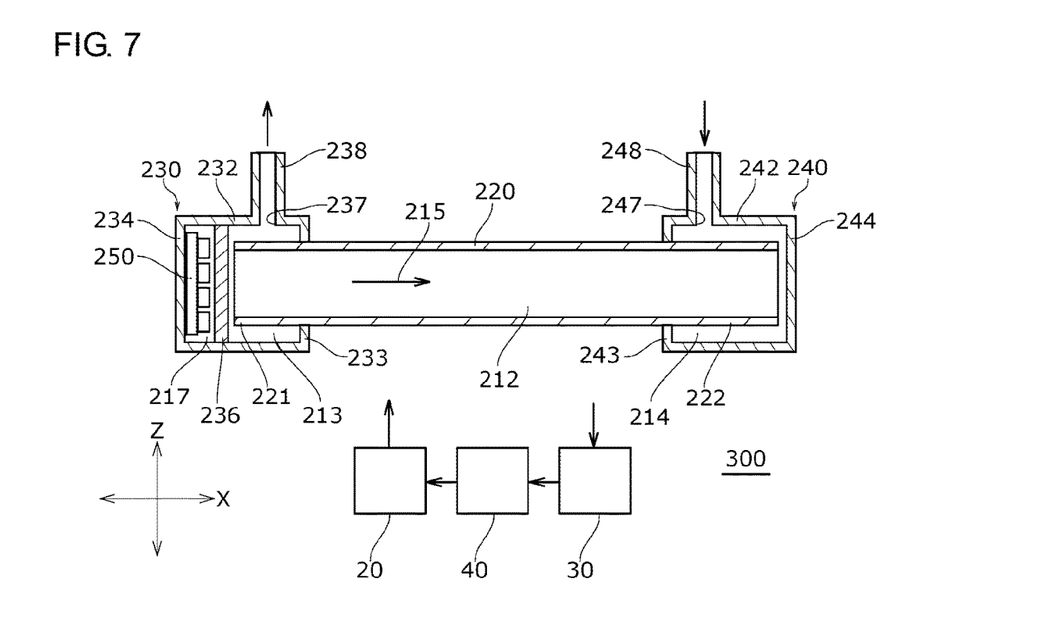
FIG. 7 is a cross-sectional view schematically showing a configuration of an irradiation device according to the first variation.

In the second embodiment, a non-limiting example where a plurality of light source units are included and ultraviolet light is radiated from both sides of the flow passage tube 220 is described. It is not essential that the light source units are provided on both sides of the flow passage tube 220. The light source unit may be provided only on one side of the flow passage tube 220. FIG. 7 is a cross-sectional view schematically showing a configuration of an irradiation device 300 according to the first variation. The irradiation device 300 according to the first variation differs from the irradiation device 200 according to the second embodiment in that the second light source unit 255 and the second window 246 are not provided, and the other features are identical. Therefore, the description of the second embodiment can be applied to the common features.

The irradiation device 300 according to the first variation provides the same function and advantage as those of the irradiation device 100 according to the first embodiment and the second irradiation device 200 according to the second embodiment owing to the features common to those of the embodiments.

(Second Variation)

Figure 8:
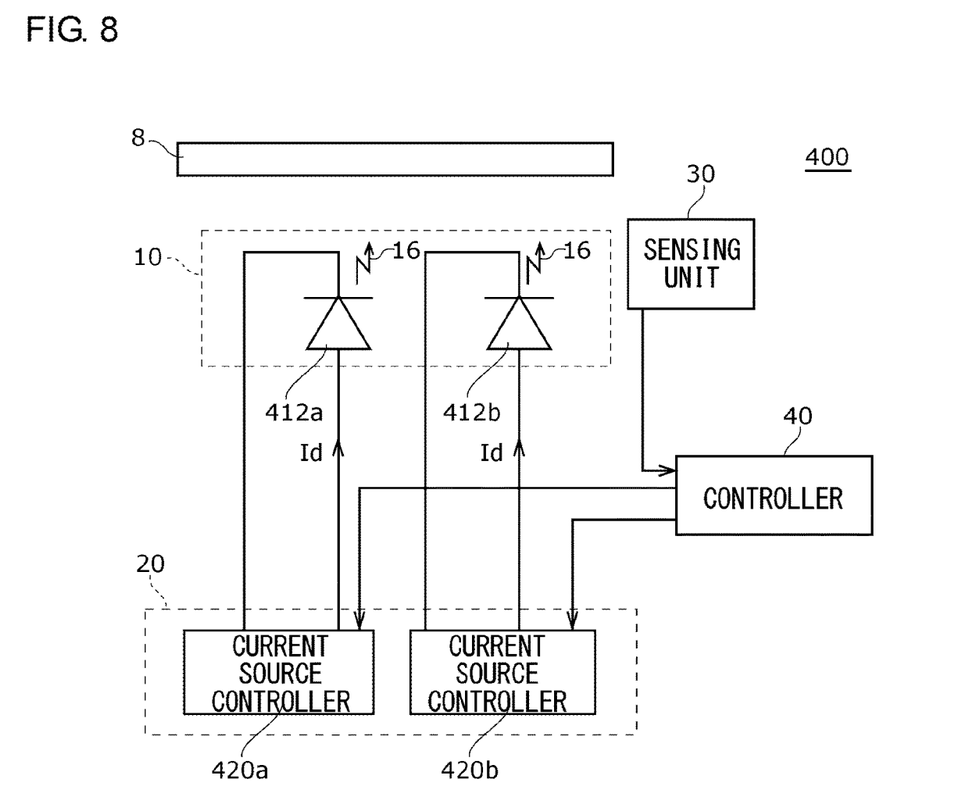
FIG. 8 is a block diagram schematically showing a configuration of an irradiation device according to the second variation.
Figure 9:
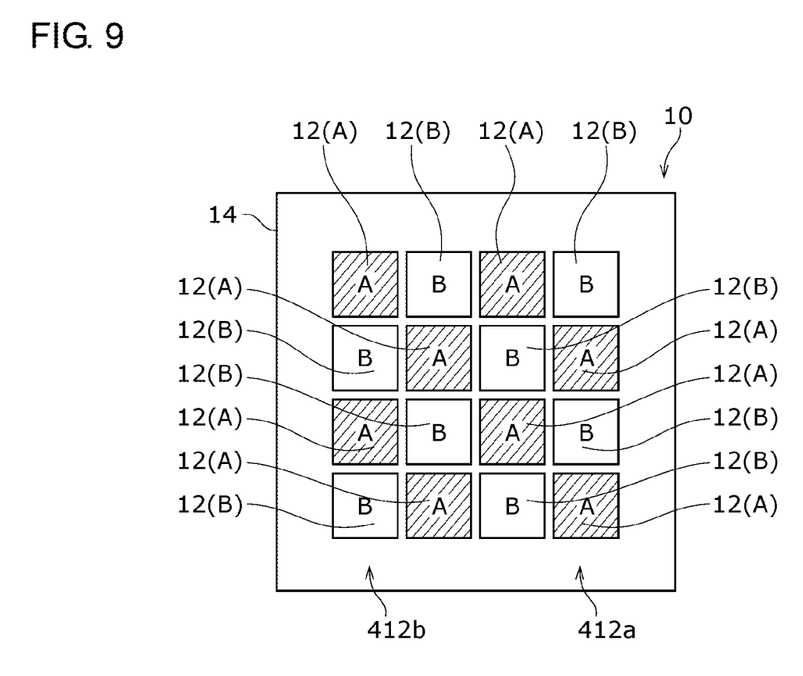
FIG. 9 schematically shows an exemplary arrangement of the light emitting devices of the irradiation device of FIG. 8.

In the first embodiment, a non-limiting example where the plurality of current sources 20b respectively corresponding to the plurality of light emitting devices 12 are included is described. For example, the plurality of light emitting devices may be organized into a plurality of (e.g., two) groups, and the light emitting devices of one of the groups may be defined as the first light emitting devices and those of the other group may be defined as the second light emitting devices. A first drive circuit for supplying a drive current to the first light emitting devices and a second drive circuit for supplying a drive current to the second light emitting devices may be provided. FIG. 8 is a block diagram schematically showing a configuration of an irradiation device 400 according to the second variation and corresponds to FIG. 1. FIG. 9 schematically shows an exemplary arrangement of the plurality of light emitting devices 12 of the light source unit 10 and corresponds to FIG. 2.

The irradiation device 400 includes the light source unit 10, the drive circuit 20, the sensing unit 30, and the controller 40 and outputs ultraviolet light as the irradiating light 16 to the target of irradiation 8. The drive circuit 20 includes a current controller 420a illustrated as exemplifying the first drive circuit and a current controller 420b illustrated as exemplifying the second drive circuit. The light source unit 10 includes a first light emitting device 412a to which the current controller 420a supplies the drive current Id and a second light emitting device 412b to which the current controller 420b supplies the drive current Id.

Each of the first light emitting device 412a and the second light emitting device 412b may comprise a single light emitting device or a plurality of light emitting devices. In the second variation, the first light emitting device 412a includes eight light emitting devices 12(A) connected in series, and the second light emitting device 412b includes eight light emitting devices 12(B) connected in series. In the second variation, the light emitting devices 12(A) and the light emitting devices 12(B) are arranged alternately on the substrate 14 in a matrix of four rows and four columns, as shown in FIG. 9.

The sensing unit 30 senses a trouble in the first light emitting device 412a and the second light emitting device 412b. When the output of the light source unit 10 is reduced due to a trouble in one of the first light emitting device 412a and the second light emitting device 412b, the controller 40 controls the drive current Id of the other of the first light emitting device 412a and the second light emitting device 412b so as to compensate the reduction in the output of the light source unit 10.

Thus, the irradiation device 400 is provided with the first system that includes the current controller 420a and controls the current in the first light emitting device 412a and the second system that includes the current controller 420b and controls the current in the second light emitting device 412b. When the light emitting device is in trouble in one of the systems, the other system can make up for it. By arranging the light emitting device 12(A) and the light emitting device 12(B) alternately, unevenness in the illuminance distribution of the light source unit 10, occurring when the light emitting device is in trouble in one of the systems, is reduced.

The configuration of the irradiation device 400 according to the second variation can be applied to the first light source unit 250 and the second light source unit 255 according to the second embodiment and to the first light source unit 250 according to the first variation.

The irradiation device 400 according to the second variation provides the same function and advantage as those of the irradiation device 100 according to the first embodiment and the second irradiation device 200 according to the second embodiment owing to the features common to those of the embodiments.

(Other Variations)

In the first embodiment, a non-limiting example where the light source unit is provided with 16 light emitting devices is described. The light source unit may be provided with two or more light emitting devices. In the first embodiment, a non-limiting example where the plurality of light emitting devices 12 are arranged in a matrix is described. The plurality of light emitting devices 12 may be arranged in an arbitrary pattern such as a concentric pattern suited to the purpose of use. These variations provide the same advantage and benefit as those of the irradiation device 100 according to the first embodiment.

Any combination of the embodiment and a variation will also be useful as an embodiment of the present invention. A new embodiment created by a combination will provide the combined advantages of the embodiment and the variation as combined.

It should be understood that the invention is not limited to the above-described embodiment but may be modified into various forms on the basis of the spirit of the invention. Additionally, the modifications are included in the scope of the invention.

What is claimed is:

1. An ultraviolet irradiation device comprising:
   a light source unit that includes a plurality of light emitting devices and outputs ultraviolet light as irradiating light;
   a drive circuit that supplies a drive current to the plurality of light emitting devices;
   a sensing unit that senses a trouble in the plurality of light emitting devices; and
   a controller that controls the drive current in accordance with a result of sensing by the sensing unit, wherein
   when an output of the light source unit is reduced due to the trouble in one or some of the plurality of light emitting devices, the controller controls the drive current of a plurality of light emitting devices other than the light emitting device in trouble so as to compensate reduction in the output of the light source unit,
   the irradiating light includes first irradiating light and second irradiating light output from mutually different positions and in mutually different directions, and
   when an output ratio between the first irradiating light and the second irradiating light changes due to the trouble in one or some of the plurality of light emitting devices, the controller controls the drive current of each of the light emitting devices so as to cancel the change in the output ratio.

2. The ultraviolet irradiation device according to claim 1, wherein
   the sensing unit is configured to sense the trouble in each of the light emitting devices in accordance with at least one of a drive current and a forward voltage of the light emitting device.

3. The ultraviolet irradiation device according to claim 1, wherein
   the sensing unit is configured to sense a failure in each of the light emitting devices in accordance with a temperature of a substrate carrying the light emitting device.

4. The ultraviolet irradiation device according to claim 1, wherein
   the sensing unit is configured to sense a failure in each of the light emitting devices in accordance with illuminance of light emitted by the light emitting device.

5. The ultraviolet irradiation device according to claim 1, wherein
   when illuminance distribution of the irradiating light changes due to the trouble in one or some of the plurality of light emitting devices, the controller controls the drive current of each of the light emitting devices so as to cancel the change in the illuminance distribution.

6. The ultraviolet irradiation device according to claim 1, wherein
   when wavelength characteristics of the irradiating light changes due to the trouble in one or some of the plurality of light emitting devices, the controller controls the drive current of each of the light emitting devices so as to cancel the change in the wavelength characteristics.

7. An ultraviolet irradiation device comprising:
   a light source unit that includes a plurality of light emitting devices and outputs ultraviolet light as irradiating light;
   a drive circuit that supplies a drive current to the plurality of light emitting devices;
   a sensing unit that senses a trouble in the plurality of light emitting devices; and a controller that controls the drive current in accordance with a result of sensing by the sensing unit, wherein when an output of the light source unit is reduced due to the trouble in one or some of the plurality of light emitting devices, the controller controls the drive current of a plurality of light emitting devices other than the light emitting device in trouble so as to compensate reduction in the output of the light source unit, the drive circuit includes a first drive circuit and a second drive circuit, the light source unit includes a first light emitting device to which the first drive circuit supplies a drive current and a second light emitting device to which the second drive circuit supplies a drive current, and when the output of the light source unit changes due to the trouble in one of the first light emitting device and the second light emitting device, the controller controls the drive current of the other of the first light emitting device and the second light emitting device so as to compensate reduction in the output of the light source unit.

8. The ultraviolet irradiation device according to claim 7, wherein
the sensing unit is configured to sense the trouble in each of the light emitting devices in accordance with at least one of a drive current and a forward voltage of the light emitting device.

9. The ultraviolet irradiation device according to claim 7, wherein
the sensing unit is configured to sense a failure in each of the light emitting devices in accordance with a temperature of a substrate carrying the light emitting device.

10. The ultraviolet irradiation device according to claim 7, wherein
the sensing unit is configured to sense a failure in each of the light emitting devices in accordance with illuminance of light emitted by the light emitting device.

11. The ultraviolet irradiation device according to claim 7, wherein
when illuminance distribution of the irradiating light changes due to the trouble in one or some of the plurality of light emitting devices, the controller controls the drive current of each of the light emitting devices so as to cancel the change in the illuminance distribution.

12. The ultraviolet irradiation device according to claim 7, wherein
when wavelength characteristics of the irradiating light changes due to the trouble in one or some of the plurality of light emitting devices, the controller controls the drive current of each of the light emitting devices so as to cancel the change in the wavelength characteristics.

* * * * *